United States Patent [19]

Ito et al.

[11] Patent Number: 4,661,320

[45] Date of Patent: Apr. 28, 1987

[54] GAS SENSOR

[75] Inventors: Kentaro Ito; Tetsuya Kubo, both of Nagano; Yukio Yamauchi, Atsugi, all of Japan

[73] Assignee: Hochiki Corporation, Tokyo, Japan

[21] Appl. No.: 636,962

[22] Filed: Aug. 2, 1984

[30] Foreign Application Priority Data

Aug. 12, 1983 [JP] Japan ............... 58-147749

[51] Int. Cl.⁴ ............................. G01N 21/01
[52] U.S. Cl. ........................ 422/86; 356/432; 422/88; 422/91
[58] Field of Search ............... 356/432–435, 356/437, 440, 445, 448; 422/83, 86, 88, 91; 436/113, 121, 139, 164

[56] References Cited

U.S. PATENT DOCUMENTS 4,484,818 11/1984 Houston ............... 356/445 X

FOREIGN PATENT DOCUMENTS 3143480 5/1983 Fed. Rep. of Germany ...... 356/437

1038840 8/1983 U.S.S.R. ............... 356/432

OTHER PUBLICATIONS

Gordon et al.; Electrochromic Attenuated Total Reflection Modulator; IBM Tech. Dis. Bull., vol. 22, No. 5, Oct. '79, p. 2074.
Spicer; Selective Ultra-Violet Photoemitter; RCA Tech. Notes. No. 520, Mar. '62.

Primary Examiner—Barry S. Richman
Assistant Examiner—Michael S. Gzybowski
Attorney, Agent, or Firm—Lackenbach Siegel Marzullo & Aronson

[57] ABSTRACT

A gas sensor comprising a device by which photo absorption is changed in the presence of hydrogen gas or hydrogen containing compound gas and an optical detecting means for detecting the change of photo absorption. The device is provided in the form of a laminate made of a metal adsorbing and dissociating hydrogen or hydrogen containing compound gas and a solid compound which is reduced by hydrogen atoms produced in the metal to change photo absorption.

13 Claims, 16 Drawing Figures

GAS SENSOR

BACKGROUND OF THE INVENTION

1. Field of the Invention

This invention relates to a gas sensor, and more particularly to a gas sensor which detects a gas by utilizing a phenomenon that a solid compound is reduced, in the presence of a small amount of hydrogen gas or hydrogen containing compound gases, by a reducing activity of hydrogen atoms dissociated and adsorbed by a catalytic metal disposed in the vicinity of the solid compound.

2. Description of Prior Art

Conventional gas sensors are generally of a contact burning type or of a semiconductor type. In a gas sensor of the contact burning type, a catalytic metal such as platinum or palladium is heated by a heater so as to cause a gas to be burned when the gas comes into contact with the metal and a change in dielectric constant caused by burning of the gas is electrically detected. In a gas sensor of the semiconductor type, the gas sensor is used in the heated state for a reason of a gas selection characteristic, response characteristic, characteristic of the device, etc. and a change in electrical characteristics caused by adsorption of the gas is detected.

However, these conventional gas sensors involve a problem of explosion because heating or burning is effected for detecting a combustible or explosive gas. Thus, the conventional gas sensors have problems in safety. Furthermore, the gas sensor of conventional type is rather poor in detection accuracy because its detected signal is electrical, thus it is a risk influence to the electric circuit which conducts the said detected signal by electromagnetic induction, for example jamming in radio wave or electrical noises.

In addition, since the device is heated, the deterioration of the device is accelerated and the characteristics of the device are bound to become unstable, which renders the reliability of the gas sensor to be lowered.

SUMMARY OF THE INVENTION

The present invention has been made with a view to obviating the above-mentioned problems involved in the conventional gas sensor.

It is therefore a first consideration of the present invention to provide a gas sensor of high reliability which is capable of stably obtaining a detection output according to a gas density, by utilizing a safe light which cannot explode or jam.

It is a second consideration of the present invention to provide a gas sensor which has excellent selection characteristics with respect to an object to be detected and which selectively detects only hydrogen gas or hydrogen containing compound gases.

It is a third consideration of the present invention to provide a gas sensor of high stability and reliability which is not changed in detection characteristics by a change with temperature or a change with time.

To accomplish the above-mentioned objects, the present invention employs a device in the form of a laminate made of a metal adsorbing and dissociating hydrogen gas or hydrogen containing compound gases and a solid compound reduced by hydrogen atoms produced in the metal, and optical means which detects a change in photo absorption of the solid compound caused by the gas adsorption.

DESCRIPTION OF THE PREFERRED EMBODIMENT

Preferred embodiments of the present invention will now be described referring to the drawings.

Figure 1:
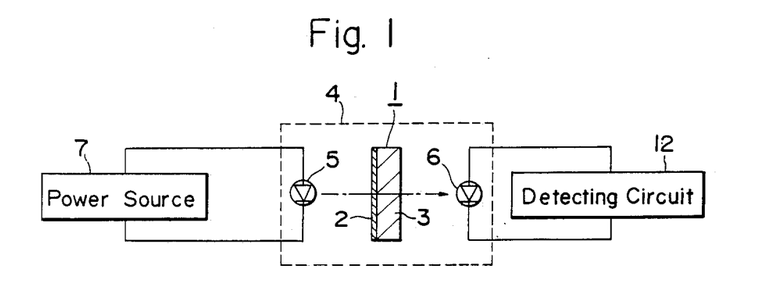
FIG. 1 is a diagrammatic view of an embodiment of the present invention.

In the drawings, numeral 1 designates a device including a metal which absorbs and dissociates hydrogen or a hydrogen containing compound as will be described in detail later. The device 1 is encased in a casing 4 which allows flow of external air thereinto. In the casing 4, a light source 5 comprising a light emitting diode and a photo detector 6 comprising a photodiode are disposed on opposite sides of the device 1 so that light from the light source 5 may enter the photodiode 6 after being transmitted through the device 1. An external power source 7 is connected to the light source 5 to drive the light source 5 to emit light continuously or pulsively. The photodiode 6 is connected to a detecting circuit 12 which electrically detects an output of the photodiode 6 corresponding to a change in the amount of transmitted light for giving an alarm when necessary.

The device 1 is made of a laminate of a catalytic metal 2 which causes dissociation of gas molecules when a gas is detected, i.e. hydrogen or a hydrogen containing compound such as hydrogen gas ($H_2$), ammonia gas ($NH_3$), hydrogen sulfide gas ($H_2S$), silane gas ($SiH_4$), etc. is brought into contact with the metal 2 to produce hydrogen atoms and a solid compound 3 which changes its photo absorption due to the reducing activity of the hydrogen atoms produced in the catalytic metal 2. As examples of the catalytic metals, there can be mentioned palladium (Pd), platinum (Pt), etc. As examples of the solid compound, there can be mentioned tungsten trioxide ($WO_3$), molybdenum trioxide ($MoO_3$), titanium dioxide ($TiO_2$), iridium hydroxide ($Ir(OH)_n$), vanadium pentoxide ($V_2O_5$), etc.

The device 1 made of a laminate of the catalytic metal 2 and the solid compound 3 is prepared for example by depositing a predetermined thickness of tungsten trioxide on a transparent glass substrate and then depositing a thin layer of palladium thereon as thin as capable of keeping the transparency of the substrate. Although the device 1 as illustrated is of two-layer laminate, it may be of a multi-layer laminate. The device 1 may be prepared by any suitable method other than deposition. For example if desired, the materials as described above may be used in mixture form, such as is in a mixture and deposited simultaneously.

The so prepared device 1 changes its photo absorption in a manner as described hereinafter. When hydrogen gas is brought into contact with the catalytic metal 2, hydrogen is adsorbed and dissociated by the metal 2. As a result, hydrogen atoms are produced in the metal 2 and these hydrogen atoms are injected into the solid compound 3. The solid compound 3 injected with proton $H^+$ produced by the catalytic metal 2 is reduced to change its concentration with respect to color and accordingly change its photo absorption. When tungsten trioxide is used for the solid compound 3 as described above, a rate of absorption is increased and the degree of the change is increased as the density of the gas increases. When hydrogen gas is thereafter decreased to null, the proton $H^+$ injected into the solid compound 3 is released therefrom and the solid compound 3 decreases its photo absorption. As a result, the device 1 restore its transparency again.

Such a photo absorption phenomenon of the device 1 as described above can be seen in relation with a reductive gas such as $NH_3$, $H_2S$, or $SiH_4$ as well as hydrogen gas. It has been confirmed by experiments that the device 1 shows sufficient response to hydrogen gas of several hundreds ppm and the speed of response after contact with hydrogen gas is rapid.

The term "photo absorption" is used in the specification to mean the phenomenon that the intensity of light is decreased after the light has travelled through a medium. The term "photo absorption rate" is used in the specification to mean a value obtained by dividing the intensity of light decreased during travelling by a predetermined distance within the medium by the original intensity of the light.

In the embodiment as illustrated in FIG. 1, gas detection is carried out in a manner as will be described below.

In a normal monitoring mode, light emitted from the light source 5 and transmitted through the device 1 is absorbed during travelling through the device 1. The absorption is predetermined by the catalytic metal 2 and the solid compound 3. The light is then incident on the photo detector 6 and a reference output is obtained by the detecting circuit 12.

In this state, if a gas to be detected enters the casing 4, hydrogen atoms are produced by dissociation of hydrogen by the catalytic metal 2 of the device 1 and the solid compound 3 is reduced by the produced hydrogen atoms. When tungsten trioxide is used as the solid compound 3, the rate of photo absorption is increased and the transmitted light amount is decreased according to the density of the gas. For this reason, the signal level of the photo detector obtained in the detecting circuit 12 is lowered. When the signal level is lowered to below a predetermined threshold value, an alarm is given.

When the device 1 using tungsten trioxide as the solid compound 3 is employed, light is absorbed in a wave range around a wave length of 14000 Å due to the reduction by hydrogen atoms. For this reason, it is desirable to use a light source which emits light having a wavelength within a range near infrared rays where the amount of absorption by the device 1 is large. Although the light from the light source 5 is passed through the device 1 only one time in the embodiment of FIG. 1, the device 1 may for example be interposed between mirrors so as to reflect the light repeatedly between the mirrors to repeatedly pass the light through the device 1 thereby to increase the change in light amount due to the photo absorption of the device 1.

Figure 2:
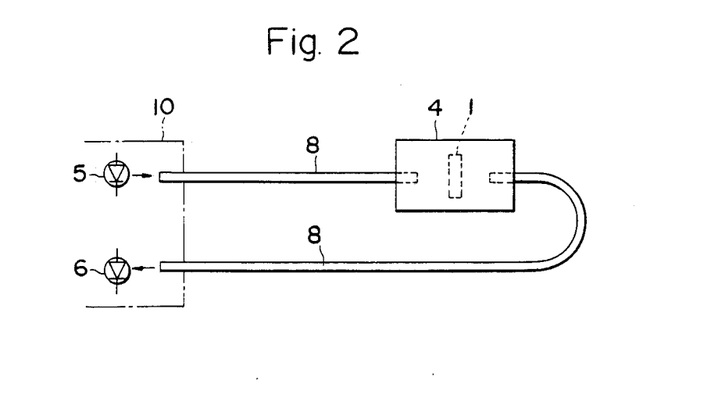
FIG. 2 is a diagrammatic view of an embodiment utilizing an optical fiber.

FIG. 2 illustrates another embodiment of the present invention wherein an optical fiber is used to form a waveguide. This embodiment enables remote gas detection.

A light source 5 and a photo detector 6 are provided in a central signal station 10 and a casing 4 and a device 1 encased therein are provided at a place where the intended gas detection is to be conducted. The light from the light source 5 is transmitted to the device 1 within the casing 4 through the optical fiber 8 and the light passed through the device 1 is also transmitted to the photo detector 6 of the central signal station 10 through the optical fiber 8.

Figure 3:
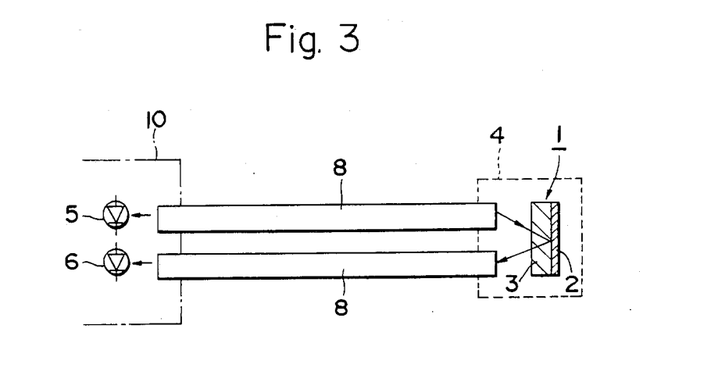
FIG. 3 is a diagrammatic view of an embodiment, utilizing a device as a reflector and an optical fiber.

In a further embodiment of the present invention as illustrated in FIG. 3, a device 1 is provided as a reflector for reflecting the light transmitted from a light source 5 through an optical fiber 8 and incident thereon and the light reflected from the device 1 is transmitted to a photo detector 6 of a central signal station 10 through the optical fiber 8. When no gas to be detected is in contact with the device 1, photo absorption by the device 1 is small so that the amount of light reflected from the device and incident on the photo detector 6 is large. When the gas to be detected enters and the photo absorption by the device is increased, the amount of reflected light incident on the photo detector 6 is decreased. Thus, the gas density is detected according to the decrease of the output of the photo detector 6.

Figure 4:
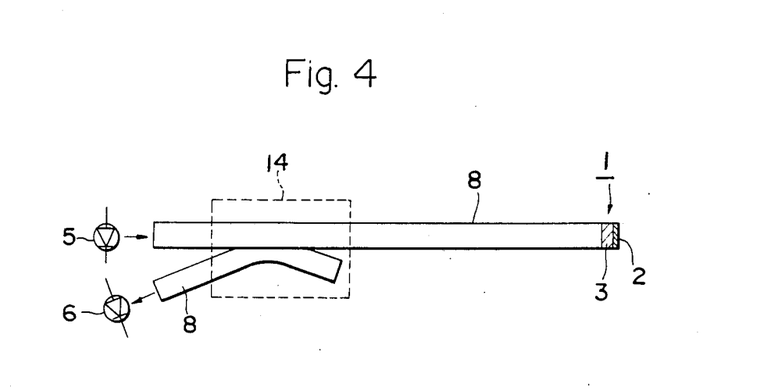
FIG. 4 is a diagrammatic view of an embodiment having a device formed directly on the end face of an optical fiber.

FIG. 4 illustrates a further embodiment of the present invention wherein a solid compound 3 such as tungsten trioxide and a catalytic metal such as palladium are directly deposited on the end face of an optical fiber 8 to form a device 1. The light emitted from a light source 5 is supplied to the device 1 on the end face of the optical fiber 8 through the fiber 8 and the light reflected from the device is allowed to enter a photo detector 6 after being separated by a directional coupler 14. When the photo absorption by the device 1 is increased by the gas to be detected, the amount of the light received by the photo detector 6 is decreased. Thus, the gas density is detected. Since the device 1 is deposited integrally on the end face of the optical fiber 8, there can be obtained a device compact in structure and capable of effecting remote monitoring.

Figure 5:
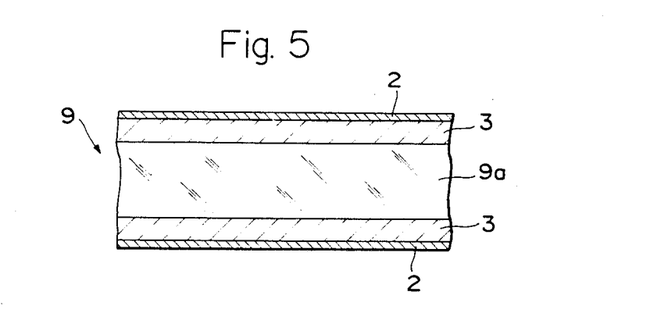
FIG. 5 is a diagrammatic sectional view of an embodiment having a device formed on the outer surface of an optical fiber.

FIG. 5 illustrates a further embodiment of the present invention wherein a solid compound 3 is deposited on the outer face of a core 9a of an optical fiber 9 and a catalytic metal 2 is further deposited on the solid compound layer 3 to form a clad on the optical fiber 9. The light from a light source 5 is passed through the core 9a and enters a photo detector 6. When no gas to be detected is in contact with the clad, the light absorption by the clad, i.e. the solid compound 3 and the catalytic metal 2, is small and the light from the light source 5 advanced while being reflected by the core 9 is conveyed efficiently so that sufficient amount of light reaches the photo detector 6. When the gas to be detected contacts the clad, hydrogen atoms produced by the catalytic metal 2 reduces the solid compound 3. If the solid compound 3 is tungsten trioxide, the rate of absorption of light is increased and the reflection rate by the clad is lowered so that the amount of light transmitted within the optical fiber 9 is decreased. The photo detector 6 detects such decrease of amount of light transmitted within the optical fiber 9.

Figure 6:
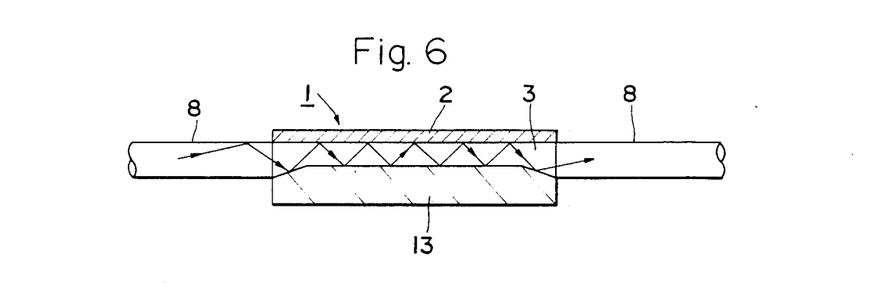
FIG. 6 is a diagrammatic view of an embodiment partly in section wherein a device is provided in the form of a thin film wave guide.

In a further embodiment of the present invention as illustrated in FIG. 6, the light travelling through an optical fiber 8 is passed through a solid compound 3 which forms a thin film wave guide.

The solid compound 3 such as tungsten trioxide and the catalytic metal such as palladium are deposited on a substrate 13 to form a device 1. The solid compound 3 constitutes a thin film wave guide having a clad consisting of the substrate 13 and the catalytic metal 2. An optical fiber 8 is connected to the opposite ends of the solid compound 3 so as to propagate the light from a light source within the thin film wave guide. In this case, the light transmitting amount by the device 1 is reduced according to the gas density due to the increase of photo absorption by the solid compound 3 caused by the gas to be detected as in the case of FIG. 5. Thus, the presence of the gas is detected.

Figure 7:
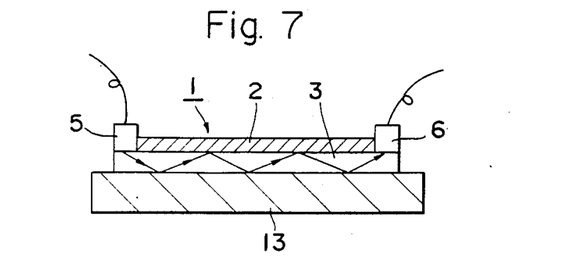
FIG. 7 is a diagrammatic sectional view of an embodiment wherein a device and an optical means are integrally formed with each other.

In a further embodiment of the present invention as illustrated in FIG. 7, a light source 5 comprising a light emitting diode and a photo detector 6 comprising a photo diode are directly provided on a device 1 and the light from the light source 5 is propagated through the thin film wave guide formed by the solid compound 3 of the device so as to enter the photo detector 6. This embodiment has an advantage that the device 1, the light source 5 and the photo detector 6 are formed integrally with each other.

Figure 8:
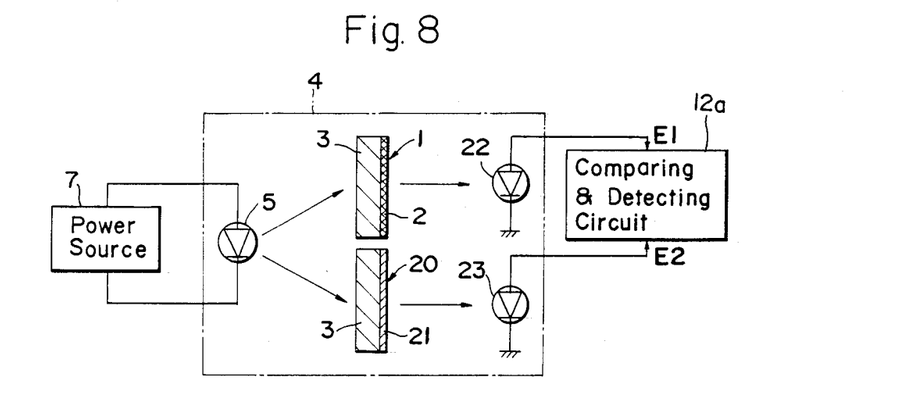
FIG. 8 is a diagrammatic view of an embodiment having two devices.

FIG. 8 illustrates a further embodiment of the present invention wherein a first device 1 and a second device 20 are disposed within a casing 4 at positions adjacent to each other so that they may be subjected to similar ambient conditions. The light from a light source 5 comprising a light emitting diode which is driven by a power source 7 is equally supplied to the first and second devices 1 and 20 so as to be transmitted therethrough.

The second device 20 comprises a solid compound 3 made of the same material as of the solid compound 3 of the first device 1, for example tungsten trioxide. The second device 20 is of a laminate structure comprising the solid compound 3 and a metal 21 which is deposited on the solid compound 3 as thin as the transparency thereof can be maintained. As the metal 21, there can be employed a metal which does not adsorb and dissociate hydrogen atoms from hydrogen gas or a hydrogen containing compound gas, such as copper, aluminum, etc.

A first detecting means comprising a photo detector 22 and a second detecting means comprising a photo detector 23 are provided at positions where the light transmitted through the first and second devices 1 and 20 are received, respectively, so as to convert the light transmitted through the first and second devices into electric signals. The detection signals from the photo detectors 22 and 23 are supplied to a comparing and detecting circuit 12a. If the detection signal from the photo detector 22 is assumed as E1 and the detection signal from the photo detector 23 is assumed as E2, the comparing and detecting circuit 12a carries out comparison detection such as $(E2-E1)/E2=Es$. When the detection output Es is above a predetermined threshold value, a gas detection output is produced.

The operation of the present embodiment will now be described. In a normal monitoring mode wherein no hydrogen gas enters the casing 4, the photo absorption rates of the solid compounds 3, 3 of the respective devices 1 and 20 are substantially the same. As substantially the same amounts of light are supplied from the light source 5 to the devices 1 and 20, the obtained detection signals E1 and E2 are substantially the same.

When hydrogen gas enters, hydrogen atoms produced by the adsorption and dissociation by the catalytic metal 2 of the first device 1 are injected into the solid compound 3 and the photo absorption is changed due to the reduction of the solid compound 3. On the other hand, the metal 21 of the second device 20 has a little adsorption and dissociation abilities and the solid compound 3 thereof is not reduced. Therefore, the photo absorption of the solid compound 3 is not changed and substantially the same transmitted light as in the normal time is incident on the photo detector 23. For this reason, when the hydrogen gas enters, the detection signal E1 by the photo detector 22 is lowered in signal level according to the gas density as compared with the reference detection signal E2 of the photo detector 23. As a result, the comparing and detecting circuit 12a detects $Es=(E2-E1)/E2$ and a detection output is obtained corresponding to the gas density. When the output becomes higher than the threshold value, a gas detection output is produced.

A compensation for a change with temperature or a change with time of the devices 1 and 20 will now be described.

When the photo absorption characteristics of the first device 1 are changed due to the influence of the ambient temperature, the photo absorption characteristics of the second device 20 which employs the solid compound 3 of the same material as of the first device 1 are changed similarly. In this case, in the normal mode where no hydrogen gas enters, there is caused no relative change in transmitted light amounts between the first and second devices 1 and 20 even if the light transmitting amounts of the first and second devices are changed by the ambient temperature. Therefore, the detection signals E1 and E2 remain substantially equal to each other irrespective of the changes by temperature. Thus, no gas detection is effected in the comparing and detecting circuit 12a.

When hydrogen gas enters, there is caused no relative change by temperature in light transmitting amounts of the first and second devices 1 and 20, too. In this case, the first device 1 brings a change in light transmitting amount which is caused both by the temperature change and the change in photo absorption by contact with hydrogen gas. The comparing and detecting circuit 12a only detects a change in the signal corresponding to the change in photo absorption rate of the device 1 caused by contact with the gas through comparison with the reference light transmitting amount of the second device 20.

The above-mentioned compensation mechanism is also applicable to the change with time. More specifically, since the first and second devices are subjected to similar change with time, the transmitted light detection signal of the first device 1 may be relatively computed with reference to the transmitted light of the second device 20 to obtain a detection output free from the influence of the change with time.

Figure 9:
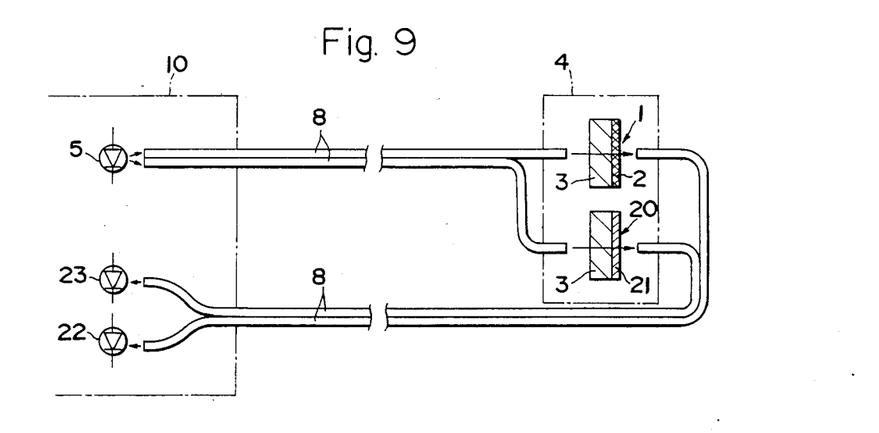
FIG. 9 is a diagrammatic view of an embodiment wherein optical fibers are provided in association with two devices, respectively.

An embodiment as illustrated in FIG. 9 is a modification of the embodiment of FIG. 8. In the embodiment of FIG. 9, a light source 5 and photo detectors 22 and 23 are provided in central signal station 10 and a first and second devices 1 and 20 are encased within a casing 4 and located at a place where gas detection is effected. The light from the light source 5 is transmitted to the devices 1 and 20 within the casing 4 through a pair of optical fibers 8, 8 and the lights transmitted through the devices 1 and 20, respectively are also transmitted through a pair of optical fibers 8, 8 so as to enter the photo detectors 22, 23, respectively. A comparing and detecting circuit 12a is also employed, but is omitted and not shown in FIG. 9.

Figure 10:
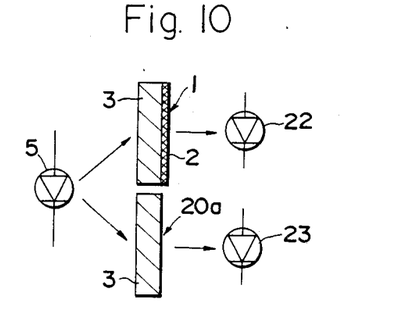
FIG. 10 is a diagrammatic view of a modification of the embodiment of FIG. 8.
Figure 11:
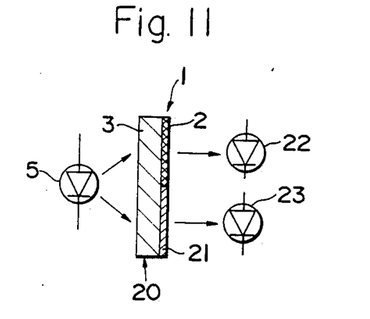
FIG. 11 is a diagrammatic view of an embodiment wherein two kinds of devices are formed integrally with each other.

FIG. 10 illustrates a further modification of the embodiment of FIG. 8 in which a second device 20a is employed instead of the second device 20 in the embodiment of FIG. 8. The second device 20a is formed only of a solid compound 3. FIG. 11 illustrates a still further modification of the embodiment of FIG. 8 wherein a catalytic metal 2 and a metal having substantially no catalytic activity are deposited on a single solid compound 3 adjacently to each other. In this embodiment, the first and the second devices 1 and 20 are provided in the form of a single device structure. The operations of these embodiments are similar to that of FIG. 8.

In the embodiments of FIGS. 8 to 11, the devices may be directly deposited on the end face of the optical fibers, the devices may be provided in the form of a clad on the optical fibers, or thin film wave guides may be provided for the devices as in the embodiments of FIGS. 5 to 7.

Figure 12:
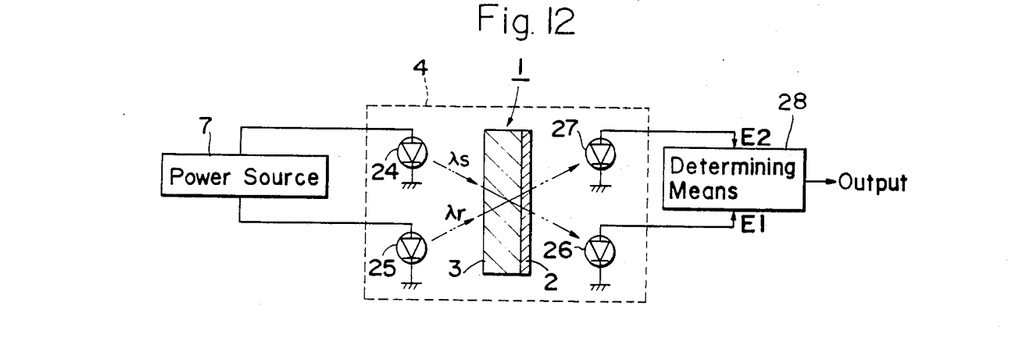
FIG. 12 is a diagrammatic view of an embodiment wherein two kinds of light of different wavelengths are employed.
Figure 13:
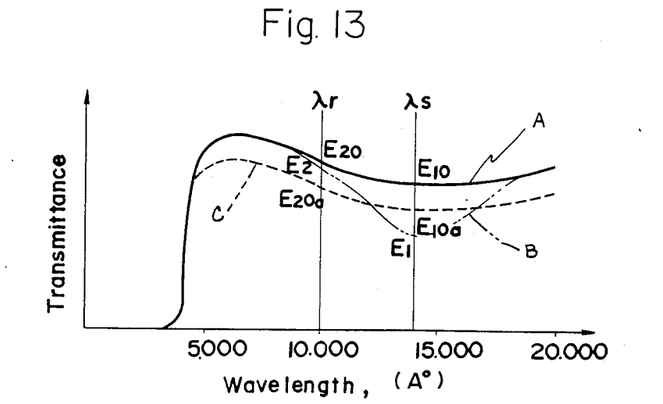
FIG. 13 is a graph showing transmittances of a device in a normal mode, in a gas detection mode, and in a miscellaneous gas contact mode, respectively.

FIG. 12 illustrates a further embodiment of the present invention which utilizes a phenomenon that the rate of photo absorption is largely changed with respect to light having a wavelength inherent of a solid compound constituting a device 1. The description will now be given referring to the fact that the photo absorption is largest around the wavelength of $\lambda s = 14{,}000$ Å when the solid compound 3 is made of tungsten trioxide. Numerals 24 and 25 designates light sources comprising light emitting diodes, respectively. The light sources 24, 25 are driven by a power source 7 continuously or intermittently and the light source 24 emits light having an energy spectrum around a wavelength $\lambda s = 14{,}000$ Å where a large change in photo absorption is caused when hydrogen gas or a hydrogen containing compound gas contacts the device as shown in FIG. 13. The light source 25 emits light having an energy spectrum around a wavelength, for example, of $\lambda r = 10{,}000$ Å as shown in FIG. 13 where photo absorption change is hardly caused even when hydrogen gas or a hydrogen containing compound gas contacts the device.

Elements 26, 27 are photo detector means comprising photo diodes, respectively, and element 28 is a determining means to which signals E1, E2 from the photo detector means 26, 27 are input. If a detection signal corresponding to the change in photo absorption of the device 1 due to contact with hydrogen gas is assumed as Es, the ratio of E1 to E2 or the ratio of the difference thereof, namely, $$Es = E1/E2 \text{ or}$$

$$Es = (E2 - E1)/E2$$

is computed. In the former case, when the detection signal Es is lower than the threshold corresponding to a predetermined gas density and in the latter case, when the detection signal Es is above the predetermined threshold value, a determination output representing the gas detection is produced.

In case where the light sources 24, 25 have light emitting characteristics of wave ranges including wavelengths $\lambda s$ and $\lambda r$, there may be employed photo detector means 26, 27 which selectively output wavelength $\lambda s$ where a change in photo absorption is large and a wavelength $\lambda r$ where a change in photo absorption is small. Alternatively, a filter may be employed to obtain the wavelength characteristics of the light sources 24, 25 and/or the photo detector means 26, 27.

The operation of the present embodiment will now be described.

In a normal time when no gas enters the casing 4, the outputs of the photo detector means 26, 27 with respect to light of wavelength $\lambda s = 14{,}000$ Å and light of wavelength $\lambda r = 10{,}000$ Å passed through the device 1 are E10 and E20, respectively as shown by a curve A in FIG. 13. The detection signal Es in the determining means 28 is initially $Eso = E10/E20$ or $Eso = (E20 - E10)/E20$.

In this state, if the gas is brought into contact with the device 1, a large photo absorption rate change is caused by the device 1 around the wavelength $\lambda s = 14{,}000$ Å as shown by curve B in FIG. 13. In contrast, there is caused no substantial change in photo absorption around the wavelength $\lambda r = 10{,}000$ Å. As a result, the detection signal Es is changed from the initial value Eso to $Ex = E1/E2$ or $Es = (E2 - E1)/E2$. When the detection signal $Es = E1/E2$ is lower than the predetermined threshold level or the detection signal $Es = (E2 - E1)/E2$ exceeds the predetermined threshold value, the determining means 28 generates a determination output representative of gas detection.

The curve A in FIG. 13 shows a transmittance of the device in relation with light of various wavelength when the device 1 is in contact with air (if a reflectance is assumed as being constant, a change in transmittance is taken as a change in absorption). The curve C shows a transmittance of the device 1 when the device is in contact with miscellaneous gases such as water vapor, alcohol, etc. More specifically, when such miscellaneous gas enters the casing 4, the transmittance of the device 1 slightly changes uniformly over the entire wavelength. Thus, there is caused no photo absorption change in the specific wavelength by the miscellaneous gases. For this reason, the detection signal Es1 due to the miscellaneous gases obtained in the determining means 28 is as follows:

$$Es1 = E10a/E20a \text{ or } E20a - E10a/E20a$$

These detection signals are substantially equal to the detection signal Eso. Thus, if the miscellaneous gases come into contact with the device, the determining means 28 does not produce false determination output corresponding to hydrogen gases or hydrogen containing compound gas.

Similarly, even if the absolute value of the absorption rate is changed with a change with time of the device 1, the determination by the determining means is not influenced.

Figure 14:
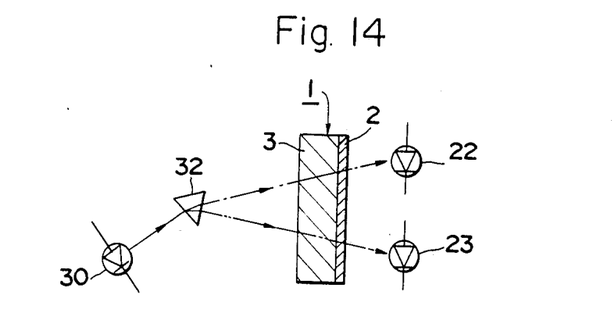
FIG. 14 is a diagrammatic view of an embodiment wherein two kinds of light are obtained by separating light by prism.

FIG. 14 illustrates an embodiment in which light from a single light source 30 is separated into its spectral components by a prism 32 before transmitted through the device 1. The light from the light source 30 is separated into light of wavelength $\lambda s$ and light of wavelength $\lambda r$ by the prism 32, passed through the device and received by photo detector means 22, 23. The outputs from the photo detector means 22, 23 are input to a determining means (not shown) as in the embodiment of FIG. 12. Thus, the determination as to the presence of the gas to be detected is made. According to the present invention, since a single light source suffices to provide desired wavelengths, the structure of the entire smoke sensor can be simplified. Furthermore, a possible error based on variations of characteristics of the light sources can be eliminated.

Figure 15:
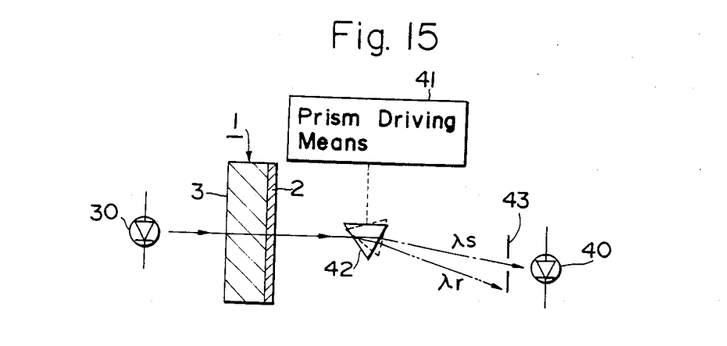
FIG. 15 is a diagrammatic view of an embodiment wherein two kinds of light are obtained by swinging a prism.

FIG. 15 illustrates a further embodiment of the present invention in which a single light source 30 and a single photo detector means 40 are employed. The light source 30 emits light within a wave range including two wavelengths $\lambda s$ and $\lambda r$. The light transmitted through the device 1 enters a prism 42 which is vibrated at a predetermined period by a prism driving means 41. The prism driving means 41 may be a bimorph piezoelectric transducer which is commonly used for a loudspeaker. The prism 42 is vibrated between a position shown by a solid line and a position shown by a broken line by the prism driving means 41. When the prism 42 is at the position of solid line, transmitted light having a wavelength of $\lambda s$ where a change of photo absorption rate is large is supplied to the photo detector means 40 through a slit 43. When the prism 42 is at the position of broken line, transmitted light having a wavelength of $\lambda r$ where a change of photo absorption rate is small is supplied to the photo detector means 40 through the slit 43. An output signal of the photo detector means 40 is input to a determining means (not shown) by sampling which is synchronized with the swing of the prism 42. In the determining means, determination of the presence of gas detection is made based on the detection signal corresponding to the ratio of the transmitted lights of wavelengths $\lambda s$ and $\lambda r$.

Figure 16:
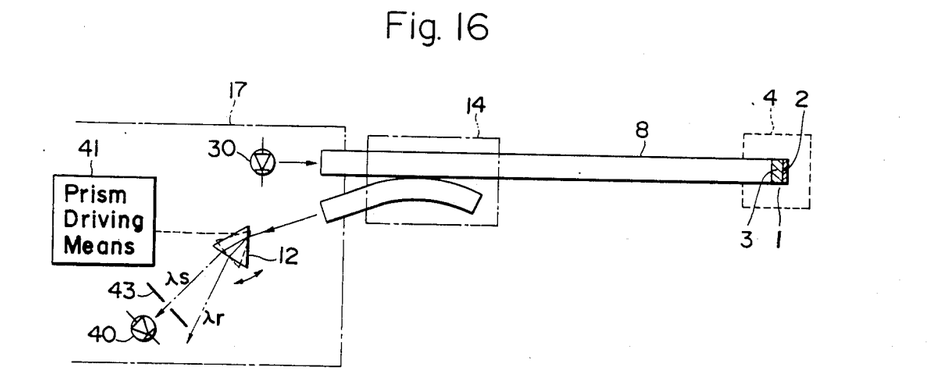
FIG. 16 is a diagrammatic view of an embodiment wherein an optical fiber is provided in addition to the arrangement of FIG. 15.

FIG. 16 illustrates a modification of the embodiment of FIG. 15 wherein a device 1 is directly deposited on the end face of an optical fiber 8. More specifically, light within a wave range including a photo absorbing wavelength $\lambda s$ and a wavelength $\lambda r$ where a change in photo absorption is small, is transmitted from a light source 30 through the optical fiber 8. The light is reflected by the device 1 formed on the end face of the optical fiber 8 and let to enter a prism 12 vibrated by a prism driving means 41 through a directional coupler 14. The light is then separated into its spectral compounds so that wavelengths $\lambda s$ and $\lambda r$ are alternately supplied to a photo detector means 40. An output signal from the photo detector means 40 is sampled by a determining means (not shown) in synchronism with the swing of the prism 42 as in the embodiment of FIG. 15. The determination as to the presence of the gas to be detected is made based on the difference between the signals corresponding to the wavelength $\lambda s$ and the wavelength $\lambda r$.

In the embodiment of FIGS. 12 to 16, the device 1 may be directly deposited on the end face of the optical fiber, the optical fiber may have a device 1 in the form of a clad, a thin film wave guide may be formed by a device 1 and a gas sensor may be prepared using these arrangement as in the embodiments of FIGS. 5 to 7.

The invention is by no means restricted to the aforementioned details which are described only as examples, they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

We claim:

1. A gas sensor which comprises a first laminate device comprising a first layer of a catalytic metal which adsorbs and dissociates hydrogen gas and other hydrogen-containing gases; and
    a second layer of a solid metal oxide compound which when subjected to reduction by hydrogen atoms produced in said catalytic metal changes its photoabsorption; and
    an optical means for detecting changes in photoabsorption of the solid metal oxide compound due to the reduction by hydrogen atoms.

2. A gas sensor according to claim 1, wherein said catalytic metal is palladium or platinum and said solid metal oxide compound is tungsten trioxide, molybdenum trioxide, titanium dioxide, iridium hydroxide, vanadium pentoxide or mixtures thereof.

3. A gas sensor according to claim 1, wherein said optical means is directly attached to said first laminate device.

4. A gas sensor according to claim 1, wherein said optical means comprises a first detecting means for monitoring light of a wavelength at which a change of photoabsorption due to reduction by the solid metal oxide compound is substantially large, a second detecting means for monitoring light of a wavelength at which a change of photoabsorption due to the reduction by the solid metal oxide compound is relatively small or negligible, and a determining means for determining presence of hydrogen gas or other hydrogen-containing compound gases based on the detection signals from said first and second detecting means.

5. A gas sensor according to claim 1, including a prism for splitting a light beam which has passed through the first laminate device and a prism driving means for rotating said prism at a predetermined period; and a slotted member for alternately transmitting a split-light beam to a detecting means, and a determining means for determining presence of hydrogen gas or other hydrogen-containing compound gases based on the input of detection signals supplied from said detecting means.

6. A gas sensor according to claim 1, wherein said laminate is of a multi-layer construction consisting of alternate layers of catalytic metal and solid metal oxide compound.

7. A gas sensor according to claim 1, which further includes a second device which consists of a solid metal oxide compound and wherein said optical means comprises a first and second detector means provided in alignment with the first and second devices, respectively, for detecting photoabsorption of the respective first and second devices and a detecting circuit for computing signals from the respective detecting means to detect the presence of hydrogen gas or other hydrogen-containing compound gases.

8. A gas sensor according to claim 1, wherein an optical fiber is disposed between said first laminate device and said optical means.

9. A gas sensor according to claim 8, wherein said first laminate device is provided in the form of a clad on said optical fiber which consists of an outer layer of catalytic metal and an inner layer of solid metal oxide compound provided on an outer surface of the optical fiber.

10. A gas sensor according to claim 8, wherein said first laminar device comprises:

an optical fiber having an intermediate thin film wave guide segment,
said thin film wave guide segment comprising:
a thin film substrate,
a layer of solid metal oxide compound, and
a layer of catalytic metal,
so disposed that the inner solid metal oxide layer and the outer catalytic metal layer form a clad on the substrate.

11. A gas sensor according to claim 1, which further includes a second laminate device which comprises a first layer of a non-catalytic metal which does not adsorb or dissociate hydrogen gas or other hydrogen-containing gases and a second layer comprising the solid metal oxide compound which comprises the second layer of the first laminate device and wherein said optical means comprises a first and second detector means provided in alignment with the first and second devices, respectively, for detecing photoabsorption of the respective first and second devices and a detecting circuit for computing signals from the respective detecting means to detect the presence of hydrogen gas or other hydrogen containing compound gases.

12. A gas sensor according to claim 7 or 11, including a prism for refracting light beam of two wavelengths, said detector means being positioned to receive said light beams.

13. A gas sensor according to claim 11, wherein the first and second devices comprise separate, adjacent portions of a single, integral piece of solid metal oxide compound whereby the catalytic metal of said first device and the non-catalytic metal of said second device are deposited adjacent one another on the same side of the single, integral piece of solid metal oxide compound.

* * * * *